United States Patent [19]

Archibald et al.

[11] 4,045,566

[45] Aug. 30, 1977

[54] PIPERIDYL-GLYCYLAMIDE DERIVATIVES

[75] Inventors: John Leheup Archibald, Windsor; John Lambert Jackson, Royston, both of England

[73] Assignee: John Wyeth & Brother Limited, Maidenhead, England

[21] Appl. No.: 676,950

[22] Filed: Apr. 14, 1976

[30] Foreign Application Priority Data

Apr. 15, 1975  United Kingdom ............... 15394/75

[51] Int. Cl.$^2$ ................... C07D 401/06; C07D 211/56
[52] U.S. Cl. ............................. 424/267; 260/293.61; 260/293.76; 260/293.77; 260/295 AM; 260/319.1; 260/326.16; 260/561 HL; 260/562 B; 260/592; 260/611 A; 260/618 D; 260/623 R; 260/623 D; 260/651 R
[58] Field of Search .............. 260/293.61, 293.76, 260/293.77; 424/267

[56] References Cited

U.S. PATENT DOCUMENTS

| | | | |
|---|---|---|---|
| 3,445,472 | 5/1969 | Archibald | 260/293.4 |
| 3,527,761 | 9/1970 | Archibald et al. | 260/293 |
| 3,655,674 | 4/1972 | Archibald et al. | 260/293.61 |
| 3,869,463 | 3/1975 | Archibald | 260/293.61 |
| 3,917,614 | 11/1975 | Cavalla et al. | 260/293.71 |

*Primary Examiner*—Cecilia M. S. Jaisle
*Attorney, Agent, or Firm*—Arthur E. Wilfond

[57] ABSTRACT

This invention relates to compounds having the general formula:

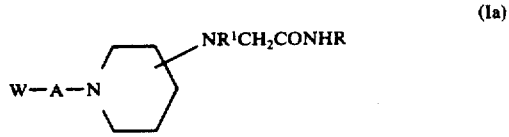

(Ia)

wherein W represents a phenyl or indolyl radical, either of which radicals may be unsubstituted or substituted by halogen, lower alkyl, lower alkoxy or hydroxy; A represents a lower alkylene radical an oxo lower alkylene radical or a hydroxy lower alkylene radical; R represents a phenyl radical optionally substituted by halogen, lower alkyl, lower alkoxy or hydroxy, or a cycloalkyl radical of 5 to 7 carbon atoms; $R^1$ represents hydrogen or a lower alkyl radical or a pharmaceutically acceptable acid addition or quaternary ammonium salt thereof; which possess hypotensive activity.

10 Claims, No Drawings

PIPERIDYL-GLYCYLAMIDE DERIVATIVES

This invention relates to novel piperidyl-glycylamide derivatives, to processes for preparing them and to pharmaceutical compositions containing them.

More particularly this invention provides compounds having the general formula

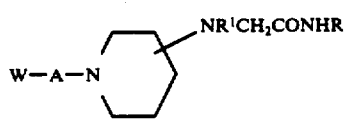
(Ia)

wherein W represents a phenyl or indolyl radical, either of which radicals may be unsubstituted or substituted by halogen, lower alkyl, lower alkoxy or hydroxy; A represents a lower alkylene radical, an oxo lower alkylene radical or a hydroxy lower alkylene radical; R represents a phenyl radical optionally substituted by halogen, lower alkyl, lower alkoxy or hydroxy, or a cycloalkyl radical of 5 to 7 carbon atoms; $R^1$ represents hydrogen or a lower alkyl radical; and the pharmaceutically acceptable acid addition or quaternary ammonium salts thereof.

The compounds of formula (Ia) form part of a general class of novel glycylamide derivatives having the general formula

(I)

wherein W represents a phenyl or indolyl radical, either of which radicals may be unsubstituted or substituted by halogen, lower alkyl, lower alkoxy or hydroxy, A represents a lower alkylene radical, an oxo lower alkylene radical or a hydroxy lower alkylene radical; R represents a phenyl radical optionally substituted by halogen, lower alkyl, lower alkoxy or hydroxy, or a cycloalkyl radical of 5 to 7 carbon atoms; $R^1$ represents hydrogen or lower

a ring system of formula

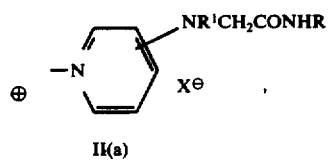

II(a)

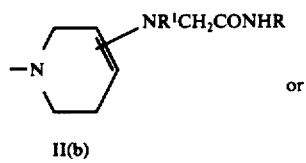

II(b)

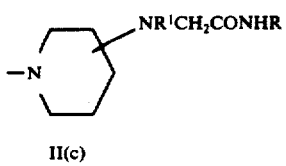

II(c)

and $X_-$ represents an anion, and the pharmaceutically acceptable acid addition or quaternary ammonium salts of those compounds containing ring system II(b) or II(c). Preferred compounds of the invention are those wherein —NR$^1$CH$_2$CONHR is in the 4-position.

By the term "lower" used in connection with the groups alkyl or alkylene is meant an alkyl or alkylene group having one to six carbon atoms, preferably 1 to 4 carbon atoms, and includes both straight and branched chains.

Examples of W are unsubstituted phenyl or phenyl substituted by one or more groups, which may be the same or different selected from halogen, (e.g., fluorine, chlorine, bromine) lower alkyl (e.g., methyl, ethyl, propyl, butyl) lower alkoxy (e.g., methoxy, ethoxy, propoxy, butoxy, or hydroxyl. Further examples of W are indolyl, e.g. indol-3-yl, which may be substituted as described above for the substituted phenyl group W. Examples of A are methylene, ethylene, propylene, butylene, oxo-ethylene, oxo-butylene, hydroxyethylene and hydroxypropylene. Examples of $R^1$ are hydrogen, methyl, ethyl, propyl and butyl. Examples of R are cyclopentyl, cyclohexyl, cycloheptyl, phenyl and phenyl substituted by the same radicals as mentioned above for the radical W when phenyl. Examples of acid addition salts are those formed from inorganic and organic acids in particular pharmaceutically acceptable acid addition salts such as the sulphate, hydrochloride, hydrobromide, hydro-iodide, nitrate, phosphate, sulphonate (such as the methane-sulphonate and p-toluene-sulphonate), acetate, maleate, fumarate, tartrate and formate. Examples of X$^-$ are halogen anions, e.g., the chloride and bromide ions. Examples of quaternary ammonium salts are those formed with lower alkyl halides, e.g., methyl bromide or benzyl halides.

The compounds of formula Ia as defined above possess hypotensive activity as demonstrated by a standard procedure involving tests on warm blooded animals. For example, 4-anilino-carbonylmethylamino-1-(4-phenyl-4-oxobutyl)-piperidine dihydrochloride, a representative compound of formula (Ia), exhibited hypotensive activity when administered intravenously to normotensive rats at dose levels of 1.6 and 3.2 mpk. Another representative compound of formula (Ia), namely 3-[2-(4-[2,6-dimethylanilinocarbonylmethylamino]--1-piperidyl)ethyl]indole, hydrochloride, showed hypotensive activity at 6.4 mpk. in a similar test.

In addition, compounds of formula I wherein

represents a pyridine or tetrahydropyridine ring system are useful as intermediates for preparing compounds of formula I wherein

represents a piperidine ring as shown hereinafter.

Particularly preferred compounds of this invention within the scope of formula Ia are compounds of general formula (Ib)

<img formula placeholder: R² substituted phenyl — A — N(piperidine)—NR¹CH₂CONHR> and pharmaceutically acceptable acid addition or quaternary ammonium salts thereof, wherein R is phenyl which may be substituted by halogen, lower alkyl, lower alkoxy or hydroxy; R¹ represents hydrogen or lower alkyl, R² represents hydrogen, halogen, lower alkyl, lower alkoxy or hydroxy; and A represents a lower alkylene, oxo lower alkylene or hydroxy lower alkylene radical; and compounds of general formula <formula (Ic): indole—A—N(piperidine)—NR¹CH₂CONHR> and pharmaceutically acceptable acid addition or quaternary ammonium salts thereof, wherein R represents a phenyl radical which may be substituted by halogen, lower alkyl, lower alkoxy or hydroxy; R¹ represents hydrogen or lower alkyl; and A represents lower alkylene, oxo lower alkylene or hydroxy lower alkylene.

This invention also provides processes for preparing the compounds of general formula I.

One such process for preparing compounds of formula I as defined above wherein

<formula: —N(ring)—NR¹CH₂CONHR> represents a ring system of formula II(a) or II(c) comprises reacting a compound of formula <formula (III): [W]—A—N(ring)—NHR¹> wherein W, R¹ and A are as defined above and

<formula: —N / NHR¹> represents a ring system of formula

<formulas IV(a) and IV(c) with X⁻> wherein X⁻ is as hereinbefore defined, with a compound of formula $$ZCH_2CONHR \qquad (V)$$

wherein R is as hereinbefore defined and Z represents halogen, e.g., chlorine or bromine. Preferably Z is chlorine. The reaction is conveniently carried out under basic conditions, for example in the presence of a tertiary amine, e.g., triethylamine, and in the presence of an inert solvent.

The compounds of formula III may be prepared according to processes described in U.K. Patent Specification Nos. 1,218,570 and 1,345,872.

A further process for preparing compounds of formula I as defined above comprises reacting a compound of general formula $$[W] - A - Y \qquad (VI)$$

wherein W and A are as defined above and Y represents a halogen atom, or an equivalent replaceable radical for example an organic sulphonyl radical such as a tosyl radical, with a compound of formula <formula VII(a)>

<formula VII(b)> or

<formula VII(c)> wherein R and R¹ are as hereinbefore defined. When a compound of formula VI is reacted with a compound of formula VII(a) according to the above then the radical Y becomes the anion X⁻ in the compound of formula I produced.

Compounds of formula VI used as starting materials in the above mentioned process are known compounds or may be prepared by known methods. Compounds of formula VII(a), VII(b) and VII(c) can generally be prepared by reacting a corresponding amino compound of formula <formula (VIII)> with a compound of formula $$ZCH_2CONHR \qquad (V)$$

wherein R and Z are as defined above and if necessary reducing the ring system to the corresponding tetrahydropyridine or piperidine ring.

Yet a further process for preparing compounds of formula I wherein

represents a ring system of formula II(b) or II(c) as defined above comprises selectively reducing a compound of formula I wherein

represents a ring system of formula II(a) or II(b) as defined above as the case may be. For example mild reduction of a compound of formula I having a pyridinium ring with an alkali metal borohydride, e.g., in methanol gives the tetrahydropyridine ring system of formula II(b). Under more vigorous reducing conditions, e.g., refluxing in isopropyl alcohol, use of an alkali metal borohydride gives the piperidine ring system of formula II(c).

Similarly catalytic hydrogenation of a compound of formula I having a pyridinium ring, for example in the presence of Raney nickel or a platinum catalyst gives the piperidine ring of formula II(c).

If a compound of formula I is prepared in which

represents the tetrahydropyridine ring system of formula II(b), this may also be reduced in like manner to the piperidine ring system of formula II(c).

If a compound of formula I is prepared in which the chain A contains a carbonyl function, then this chain may be selectively reduced. For example, when A is the —CO—CH$_2$— residue this may be reduced with an alkali metal borohydride to give the

residue. When the residue is reduced under more drastic conditions, the ethylene chain —CH$_2$—CH$_2$— results.

A still further process for preparing compounds of formula I comprises reacting a compound of formula

(IX)

wherein W, A and R$^1$ are as hereinbefore defined, M represents a halogen or an alkoxy group, preferably a lower alkoxy group, and

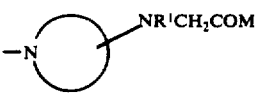

represents a ring system of formula

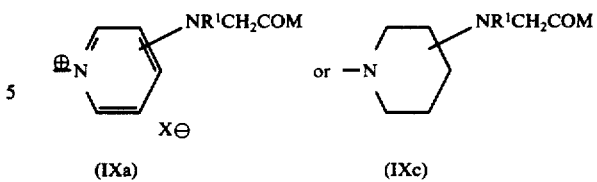

(IXa) (IXc)

wherein X is as hereinbefore defined, with a compound of formula:

$$H_2NR \qquad (X)$$

wherein R is as hereinbefore defined. M is preferably chlorine or a methoxy or ethoxy group. Compounds of formula IX wherein M is an alkoxy group used in the reaction above may be prepared by reacting a corresponding compound of formula (III) with a compound of formula $$ZCH_2COM \qquad (XI)$$

wherein Z is a halogen and M is an alkoxy group. Compounds of formula IX wherein M is halogen may be prepared by hydrolysing compounds of formula IX wherein M is an alkoxy group and then reacting the acid produced with a halogenating agent, e.g., PCl$_5$, SOCl$_2$.

If necessary, in any of the reactions hereinbefore described, reactive substituent groups may be blocked during a reaction and released at a later stage. As already indicated the novel tetrahydropyridine and piperidine compounds provided by the invention contain a basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

A further aspect of this invention is the provision of a pharmaceutical composition comprising a compound of formula I as defined above wherein

represents a ring system of formula II(c) or a pharmaceutically acceptable salt thereof together with a pharmaceutically acceptable carrier.

Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or suboutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 5 mg. of less to 500 or more, according to the particular need and the activity of the active ingredient. The invention also includes the compounds in the absence of carrier where the compounds are in unit dosage form.

The following non-limiting Examples illustrate the invention. Temperatures are in degrees Centigrade.

EXAMPLE 1

4-Anilinocarbonylmethylamino-1-(4-phenyl-4-oxobutyl) piperidine.

4-Amino -1-(4-phenyl-4-oxobutyl) piperidine dihydrochloride (1.75g) was suspended in dimethylformamide (15 ml) containing triethylamine (3 ml) and chloroacetanilide (0.85G) added. The mixture was stirred for 48 hours and the precipitate of $Et_3N.HCl$ filtered off. The filtrate was poured into water and the solid product filtered off and recrystallised from $EtOH/H_2O$ to give the title compound (1.35g). This was converted to the hydrochloride (1.35g) by treatment with EtOH-HCl and $Et_2O$, m.p. 255.1°.

Analysis: Found C, 58.91; H, 6.73; N, 8.75; $C_{23}H_{29}N_3O_2.2HCl.H_2O$
requires: C, 58.74; H, 7.07; N, 8.93%.

EXAMPLE 2

4-(2,6-Dimethylanilinocarbonylmethylamino)-1-(4-phenyl-4-oxobutyl) piperidine

4-Amino-1-(4-phenyl-4-oxobutyl) piperidine dihydrochloride (1.75g) was condensed with N-(2,6-dimethylphenyl) chloroacetamide (0.999) in the manner of Example 1 to give the title compound which was converted to the hydrochloride salt (1.85g), m.p. 276.8°
Analysis: Found, C, 62.26; H, 7.48; N, 8.68; $C_{25}H_{33}N_3O_2.2HCl$ requires C, 62.25; H, 7.34; N, 8.75%

EXAMPLE 3

3-[2-(4-Anilinocarbonylmethylamino-1-piperidyl) ethyl]indole

3-[2-(4-Amino-1-piperidyl) ethyl]indole hydrate (1.31g.) was dissolved in dimethylformamide (15 ml) containing triethylamine (2 ml) and chloroacetanilide (0.85g) added. The mixture was stirred for 24 hours, poured into water (100 ml) and extracted with chloroform (2 × 50 ml). The combined chloroform layers were washed with water, dried ($MgSO_4$), filtered and evaporated to give the title compound as an amber oil (2.06 g). This was converted to the hydrochloride (1.29 g), m.p. 240.7°, on addition of EtOH-HCl and $Et_2O$.
Analysis; C, 61.37; H, 6.77; N, 12.12; $C_{23}H_{28}N_4O.2HCl$;
requires C, 61.47; H, 6.73; N, 12.47%.

EXAMPLE 4

3-[2-(4-]2,6-Dimethylanilinocarbonylmethylamino]-1-piperidyl) ethyl]indole

3-[2-(4-Amino-1-piperidyl) ethyl]indole hydrate (1.31g) was condensed with N-(2,6-dimethylphenyl) chloracetamide (0.999) in the manner of Example 3 to give the title compound which was converted to the hydrochloride (2.03g), m.p. 203.2°.
Analysis: Found C, 60.49; H, 7.40; N, 10.93.
$C_{25}H_{32}N_4O.2HCl.H_2O$ requires C, 60.60 H, 7.32; N, 11.31%.

EXAMPLE 5

4-{[N-Methyl-N-anilinocarbonylmethyl]amino}-(4-phenyl-4-oxobutyl) piperidine.

Using a procedure analogous to Example 1 4-[N-methylamino]-1-(4-phenyl-4-oxobutyl) piperidine may be reacted with chloroacetanilide to give the title compound.

EXAMPLE 6

4-Anilinocarbonylmethylamino-1-(4-phenyl-4-hydroxybutyl)-piperidine.

4-Anilinocarbonylmethylamino-1-(4-phenyl-4-oxobutyl) piperidine may be reduced using sodium borohydride to give the title compound.

EXAMPLE 7

4-p-Chloroanilinocarbonylmethylamino-1-(4-phenyl-4-oxybutyl)-piperidine

Using a procedure analogous to Example 1, 4-amino-1-(4- phenyl-4-oxobutyl) piperidine may be reacted with N-(p-chlorophenyl) chloracetamide to give the title compound.

EXAMPLE 8

4-p-Methylanilinocarbonylmethylamino-1-(4-phenyl-4-oxobutyl) piperidine

Using a procedure analogous to Example 1 4-amino-1-(4-phenyl-4-oxobutyl) piperidine may be reacted with N-(p-tolyl) chloro-acetamide to give the title compound.

EXAMPLE 9

4-p-Methoxyanilinocarbonykmethylamino-1-(4-phenyl-4-oxobutyl) piperidine

Using a procedure analogous to Example 1, 4-amino-1-(4-phenyl-4-oxobutyl) piperidine may be reacted with N-(p-methoxyphenyl) chloroacetamide to give the title compound.

EXAMPLE 10

4-p-Hydroxyanilinocarbonylmethylamino-1-(4-phenyl-4-oxobutyl) piperidine 4-p-Methoxyanilinocarbonylmethylamino-1-(4-phenyl-4-oxobutyl)-piperidine may be reacted with pyridine hydrochloride to give the title compound.

EXAMPLE 11

2-[1-(3-Benzoylpropyl)-4-piperidinylamino]-N-cyclohexylacetamide

Using a procedure analogous to Example 1 4-amino-1-(4-phenyl-4-oxobutyl) piperidine may be reacted with N-cyclohexylchloracetamide to give the title compound.

We claim

1. A compound having the general formula:

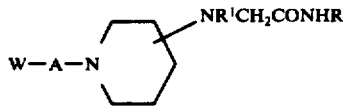

(Ia)

wherein W represents a phenyl or 3-indolyl radical, either of which radicals may be unsubstituted or substituted by halogen, lower alkyl, lower alkoxy or hydroxy; A represents a lower alkylene radical, an oxo lower alkylene radical or a hydroxy lower alkylene radical; R represents a phenyl radical optionally substituted by halogen, lower alkyl, lower alkoxy or hydroxy, or a cycloalkyl radical of 5 to 7 carbon atoms radical; R¹ represents hydrogen or a lower alkyl radical; or a pharmaceutically acceptable acid addition or quaternary ammonium salt thereof.

2. A compound as claimed in claim 1 having the general formula

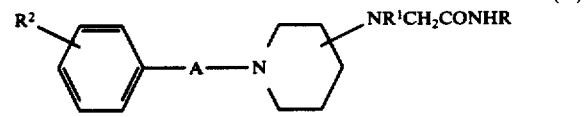

(Ib)

or a pharmaceutically acceptable acid addition or quaternary ammonium salt thereof, wherein R represents phenyl which may be substituted by halogen, lower alkyl, lower alkoxy or hydroxy; R¹ represents hydrogen or lower alkyl, R² represents hydrogen, halogen, lower alkyl, lower alkoxy or hydroxy; and A represents a lower alkylene, oxo lower alkylene or hydroxy lower alkylene radical.

3. A compound as claimed in claim 1 having the general formula:

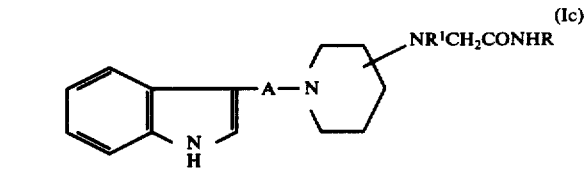

(Ic)

or a pharmaceutically acceptable acid addition or quaternary ammonium salt thereof, wherein R represents a phenyl radical which may be substituted by halogen, lower alkyl, lower alkoxy or hydroxy; R¹ represents hydrogen or lower alkyl, and A represents lower alkylene, oxo lower alkylene or hydroxy lower alkylene.

4. A compound as claimed in claim 2 wherein A represents a —COCH₂CH₂CH₂— radical.

5. A compound as claimed in claim 3 wherein A is an ethylene radical.

6. A compound as claimed in claim 1 which is 4-anilinocarbonylmethylamino-1-(4-phenyl-4-oxobutyl)-piperidine.

7. A compound as claimed in claim 1 which is 4-(2,6-dimethylanilinocarbonylmethylamino)-1-(4-phenyl-4-oxobutyl) piperidine.

8. A compound as claimed in claim 1 which is 3-[2-(4-anilinocarbonylmethylamino-1-piperidyl) ethyl]-indole.

9. A compound as claimed in claim 2 which is 3-[2-(4-[2,6-dimethylanilinocarbonylmethylamino]-1-piperidyl)ethyl]indole.

10. A hypotensive pharmaceutical composition comprising a therapeutically effective amount of a compound as claimed in claim 1 or a pharmaceutically acceptable acid addition or quaternary ammonium salt thereof together with a pharmaceutically acceptable carrier.

* * * * *